United States Patent [19]

Burk et al.

[11] Patent Number: 4,954,891
[45] Date of Patent: Sep. 4, 1990

[54] LIGHT GUIDED ILLUMINATING/SECTIONING DEVICE FOR SHEET INSPECTION SYSTEM

[75] Inventors: Gary N. Burk, Columbus; Thomas O. McCanney, Sunbury; Paul Williams, Columbus, all of Ohio

[73] Assignee: Process Automation Business, Inc., Columbus, Ohio

[21] Appl. No.: 300,089

[22] Filed: Jan. 23, 1989

Related U.S. Application Data

[63] Continuation-in-part of Ser. No. 217,395, Jul. 11, 1988, abandoned.

[51] Int. Cl.⁵ .............................................. H04N 7/18
[52] U.S. Cl. ................................... 358/101; 362/223
[58] Field of Search ............... 358/101, 106, 107, 473, 358/474, 495; 356/429, 430; 362/31, 223; 355/1, 70; 250/571, 578

[56] References Cited

U.S. PATENT DOCUMENTS

| 4,186,431 | 1/1980 | Engel et al. ........................ 362/223 |
| 4,248,517 | 2/1981 | Nishikawa ............................... 355/1 |
| 4,492,477 | 1/1985 | Leser . | |
| 4,536,830 | 8/1985 | Wisniewski ........................ 362/223 |
| 4,580,200 | 4/1986 | Hess et al. ........................... 362/223 |
| 4,616,267 | 10/1986 | Horikawa ....................... 358/474 X |
| 4,654,765 | 3/1987 | Laidman ........................ 362/223 X |
| 4,675,730 | 6/1987 | Adomaitis et al. . | |
| 4,714,340 | 12/1987 | Stillwagon ..................... 356/430 X |

FOREIGN PATENT DOCUMENTS

0076678  6/1981  Japan .................................. 358/475
0041364  3/1985  Japan .................................. 358/475

Primary Examiner—James J. Groody
Assistant Examiner—Victor R. Kostak
Attorney, Agent, or Firm—Killworth, Gottman, Hagan & Schaeff

[57] ABSTRACT

A light source module for use with a multi-camera array in a video surface inspection system includes a first light emitter which extends lengthwise across the entire width of a sheet to be inspected. Light from the first light emitter, which preferably comprises one or more fluorescent lamps, is received by a light guide and carried by the guide to uniformly illuminate a band extending entirely across the width of the moving sheet. The light guide comprises a transparent thermoplastic such that the light receiving end of the guide can be bent to define a plurality of sections which can be axially aligned with a corresponding plurality of fluorescent lamps. The fluorescent lamps may be powered by individual inverter ballasts which may be driven inturn by one or more variable dc power supplied to control the intensity of light emitted by the lamps. The light source module can also assist the inspection system in overcoming redundant data processing problems by providing second light emitters which illuminate the sheet in overlapping portions of the field of view of adjacent cameras of the multi-camera array to define data dividing points. Accordingly, duplicated data generated by the video cameras can be divided among the cameras at the defined data dividing points such that duplicated data is only processed once by the video surface inspection system.

25 Claims, 2 Drawing Sheets

LIGHT GUIDED ILLUMINATING/SECTIONING DEVICE FOR SHEET INSPECTION SYSTEM

BACKGROUND OF THE INVENTION

This application is a continuation-in-part of U.S. patent application Ser. No. 217,395, filed July 11, 1988, now abandoned.

The present invention relates generally to a system for inspecting a surface of moving sheet material and, more particularly, to a light source module for use with a multi-camera imaging system to inspect such moving sheet material.

Video surface inspection systems are known for monitoring the surface of a moving object, for example, a moving sheet of material to detect defects in the surface of the sheet. For example, see U.S. Pat. No. 4,675,730, wherein a portion of a sheet of moving material extending entirely across the width of the material is illuminated and monitored by a multi-camera array. In such video surface inspection systems, non-uniformity of the light system used to illuminate the moving sheet of material has led to difficulties in processing the signals from the camera.

Problems arise since the cameras must be set such that they do not overdrive for the highest levels of illumination and yet can recognize the lowest levels of illumination. Further, since such sheet materials can be moving at speeds in excess of 4500 feet per minute (fpm), real time processing of the video signals generated by the multi-camera array monitoring the illuminated portion of the sheet material can create data processing problems. Such data processing problems are aggravated by overlaps in the fields of view of the individual cameras making up the multi-camera array, which overlaps are required to ensure inspection of the entire sheet. The aggravation caused by the overlaps of the fields of view of the cameras is apparent when it is realized that each of the cameras generates data which is redundant in that the camera or cameras immediately adjacent thereto generate identical portions of data corresponding to the overlap(s).

Accordingly, the data processing system which is already faced with an extensive processing task in responding to pertinent data received from the cameras of the multi-camera array, must also process redundant data. By processing this redundant data, a potentially over-burdening task is placed on the computer, and in any event, the absolute maximum speed of sheet material which can be inspected is reduced.

In view of these problems, there is a need for a light source for video surface inspection systems which can provide uniform illumination of a band or strip extending entirely across the width of a sheet to be monitored and, if such light source could further assist in the identification of redundant data and hence the elimination of processing which is otherwise required for such redundant data, it would serve to greatly assist and advance the art of video surface inspection systems.

SUMMARY OF THE INVENTION

The problems of prior art video surface inspection systems with regard to uniformity of illumination are overcome in accordance with the present invention which also assists in reducing data processing time by eliminating processing of redundant data generated by overlapping fields of view of cameras of multi-camera arrays used in such systems. In the present invention, a light source module for use with a multi-camera array includes a first light emitter which extends lengthwise across the entire width of a sheet to be inspected. Light from the first light emitter is received by a light guide and carried by the guide to illuminate a portion of the moving sheet extending entirely across its width with a uniform light.

To assist in overcoming processing problems by substantially eliminating the processing of redundant data in video surface inspection systems incorporating the light source module of the present invention, second light emitters are utilized to illuminate the sheet in a number of discontinuous regions corresponding to overlaps in the fields of view of adjacent cameras of the multi-camera array. The light generated by the second light emitters can be detected to define dividing points in the overlapping fields of view. Thus, data generated by cameras having overlapping fields of view can be divided between the cameras. Data generated to one side of the detected light by one of the cameras is processed while data generated to the other side of the detected light by the same camera is not processed but is accounted for by processing corresponding data which is generated by the camera adjacent thereto. In this way, the processing of redundant data generated by adjacent cameras is eliminated.

In accordance with one aspect of the present invention, a light source module for use with a multi-camera array to inspect a moving sheet of material comprises first light emitter means for emitting light in response to applied power with the first light emitter means extending lengthwise across the entire width of a sheet to be inspected with width being defined in a direction transverse to the direction of sheet movement. Housing means are provided for supporting the first light emitter means with the housing means extending lengthwise across a distance greater than the entire width of the sheet to be inspected. Light guide means are secured to the housing means for receiving light from the first light emitter means and guiding that light toward a sheet to be inspected such that the sheet is illuminated over a portion or band thereof extending across its entire width. The light guide means includes a light receiving surface facing the first light emitter means and a light ejecting surface facing the sheet. Preferably the light guide means is composed of transparent thermoplastic such as Plexiglas. The light source module may also comprise light control means connected to the first light emitter means for controlling the intensity of light emitted.

In the illustrative embodiment, the first light emitter means comprises at least one generally cylindrical fluorescent lamp having terminals on each end thereof. For the inspection of wide sheets of material, the first light emitter means may comprise a plurality of such fluorescent lamps with the lamps being positioned in the housing means such that they axially extend in substantially the same direction and the ends of adjacent pairs of lamps overlap at least to a degree corresponding to the length of terminals at the ends of the lamps. When fluorescent lamps are used as the first light emitter means, the light control means may comprise an inverter ballast and a variable dc power supply for driving the inverter ballast.

Preferably, the fluorescent lamp or lamps are phosphor-coated over a first circumferential range thereof but not phosphor-coated over a second circumferential range. When a plurality of fluorescent lamps are utilized in the light source module, the light receiving surface of the light guide means comprises a plurality of separate sections with each of the sections facing one of the plurality of fluorescent lamps and extending lengthwise in the axial direction of that lamp.

The light source module of the present invention may further comprise second light emitter means for emitting light in response to applied power which light illuminates the sheet to be inspected in each of a plurality of discontinuous regions corresponding to overlaps in the fields of view of adjacent cameras of the multi-camera array. The second light emitter means may comprise a plurality of light emitting diodes or a plurality of optical fibers which conduct light to illuminate the plurality of discontinuous regions.

By constructing the light guide means of transparent thermoplastic material, such as Plexiglas, the light guide means can be conveniently sectioned with alternating sections being bent to define the plurality of separate sections making up the light receiving surface of the light guide means. Such formation of the light guide means facilitates overlap of adjacent pairs of fluorescent lamps since it permits pairs of adjacent lamps to be offset axially from one another yet parallel to one another to provide uniform light conveyance via the light guide means to a moving sheet of material to be inspected.

It is therefore an object of the present invention to provide a light source module for use with a multi-camera array in a video surface inspection system which provides uniform illumination of a portion of a sheet to be inspected across its entire width to thereby simplify processing of camera signals which can otherwise be complicated due to nonuniform illumination; to provide a light source module for use with a multi-camera array in a video surface inspection system which provides uniform illumination of a portion of a sheet to be inspected across its entire width wherein the intensity of the uniform illumination can be varied as required; and, to provide a light source module for use with a multi-camera array in a video surface inspection system which provides uniform illumination of a portion of a sheet across its entire width which module further provides for identifying locations within overlapping regions of the fields of view of the cameras substantially eliminate processing of redundant data generated by the cameras due to the overlapping fields of view which are necessary to ensure inspection of the entire sheet of material.

Other objects and advantages of the invention will be apparent from the following description, the accompanying drawings, and the appended claims.

DETAILED DESCRIPTION OF THE INVENTION

Figure 1:
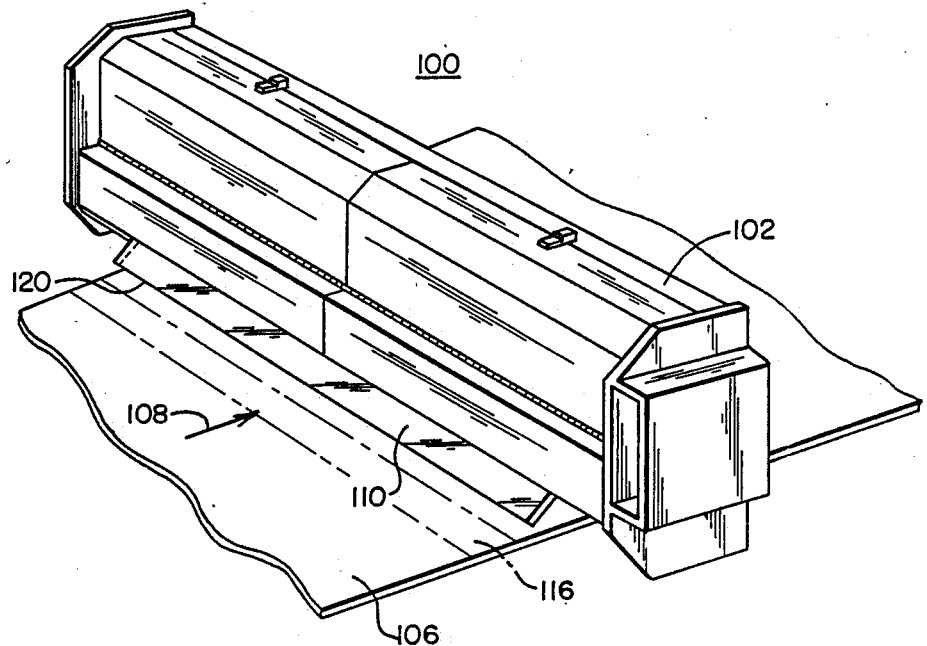
FIG. 1 is a perspective view of a light source module in accordance with the present invention.
Figure 2:
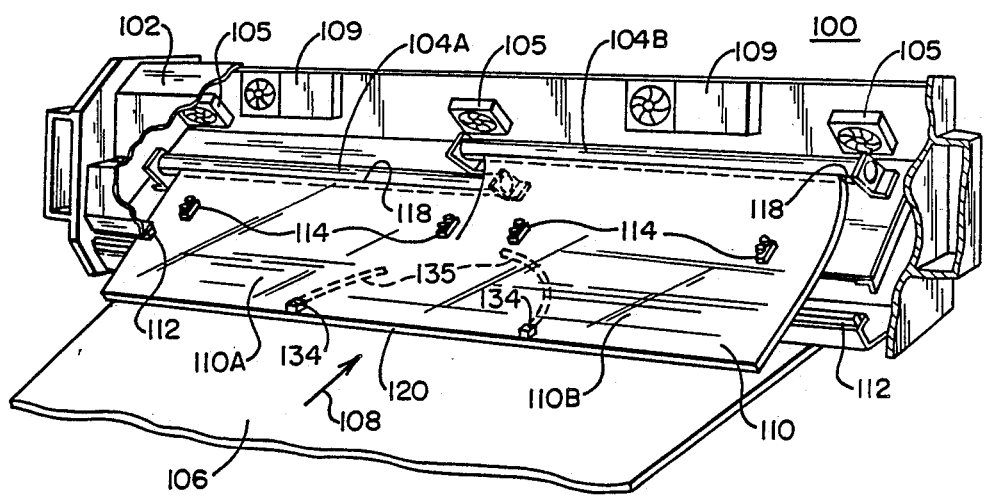
FIG. 2 is a broken-away perspective view of the light source module of FIG. 1 showing the internal components of the light source module.

A perspective view of a light source module 100 in accordance with the present invention for use with a multi-camera array in a video surface inspection system is shown in FIG. 1 with portions of a housing 102 being broken away in FIG. 2 to reveal the components of the light source module 100. First light emitter means comprising tubular fluorescent lamps 104 in the preferred embodiment provide for emitting light in response to applied power. Cooling fans 105 may be provided, if necessary, to control the operating temperature of the light source module 100.

The fluorescent lamps 104 extend lengthwise across the entire width of a sheet 106 to be inspected with the width of the sheet 106 being measured in a direction transverse to the direction of sheet movement indicated by an arrow 108. Inverter ballasts 109 are connected to operate the fluorescent lamps 104 at high frequencies to provide flicker-free light as is well known in the art. Such inverter ballasts are driven by a dc power supply (not shown) and are commercially available from The Bodine Company of Collierville, Tenn.

If a variable intensity light source is desired, the inverter ballasts 109 can be driven by a variable dc power supply (not shown) which can be controlled, for example, to maintain the light intensity from the fluorescent lamps at a desired value as the fluorescent lamps 104 age. A variable dc power supply having a dc voltage range of 0-100 volts dc permits operation of the fluorescent lamps at frequencies up to approximately 38 khz. Housing means comprising the housing 102 in the illustrative embodiment extends lengthwise across a distance greater than the entire width of the sheet 106 to be inspected and provides for supporting the fluorescent lamps 104, the cooling fans 105 and the inverter ballasts 109.

Light guide means comprising a transparent thermoplastic light guide 110 is secured to the housing 102 by means of clamping bars 112 and support members 114 or other means as will be apparent to those skilled in the art. The light guide 110 receives light from the fluorescent lamps 104 and guides the received light toward the sheet 106 to be inspected such that the sheet 106 is illuminated over a portion thereof indicated schematically by the numeral 116 in FIG. 1 which extends across its entire width. The light guide 110 has a light receiving surface 118 facing the fluorescent tubes 104 and a light ejecting surface 120 facing the sheet 106 to be inspected.

The light guide 110 is composed of a transparent thermoplastic material, preferably Plexiglas, such that sections of the light guide 110 can be deformed to accommodate two or more fluorescent lamps 104 with a single light guide when wide sheets of material are to be inspected. Plexiglas is preferred because it has a refractive index which tends to retain light within the light guide 110 when the light guide 110 is surrounded by air. Thus, as shown in FIG. 2, the light guide 110 can be divided into a plurality of separate sections with each of the sections facing one of a plurality of fluorescent lamps and extending lengthwise in the axial direction of that lamp.

As shown in FIG. 2, the light guide 110 comprises two sections, 110A and 110B with section 110A being substantially planar and aligned with the fluorescent lamp 104A whereas the second section 110B has been deformed by curving its portion of the light receiving surface 118 upwardly such that it is aligned with the fluorescent lamp 104B. While the light guide 110 has been divided into two sections 110A and 110B in FIG. 2, it should be apparent that any number of sections desired or required to accommodate a defined sheet width to be inspected can be formed in accordance with the present invention.

Figure 5:
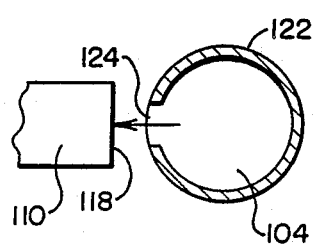
FIG. 5 is a sectional view of the fluorescent tube of FIG. 4 taken along the section line 5—5.
Figure 4:
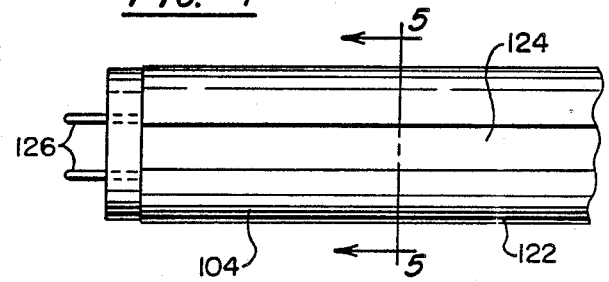
FIG. 4 is a broken-away end section of a fluorescent tube especially constructed for use in the light source module of the present invention.

Portions of the fluorescent lamps 104 are shown in FIGS. 4 and 5. As shown in FIG. 4, the fluorescent lamps 104 are phosphor-coated over a first circumferential range 122 but no phosphor-coated over a second circumferential range 124. Such fluorescent lamps are specially constructed by Perry Thrasher of Light Sources Inc. of New Jersey and further provide a heavy phosphor coating over the circumferential range 122 while leaving the circumferential range 124 uncoated. This construction provides a slotted or slit structure such that light generated within the fluorescent lamp 104 is concentrated and passes through the uncoated strip defined by the circumferential range 124.

Each of the fluorescent lamps 104 have terminals 126 on each end of the lamp as shown in FIG. 4. To ensure that a uniform illumination is provided by the light source module 100, the fluorescent lamps 104 are positioned in the housing 102 such that they axially extend in substantially the same direction and that the ends of adjacent pairs of the lamps overlap at least to a degree corresponding to the length of the terminals 126. By thus arranging the fluorescent lamps 104, only the fluorescing central portions extending between the terminals 126 are exposed to the light receiving surface 118 of the light guide 110.

Figure 3:
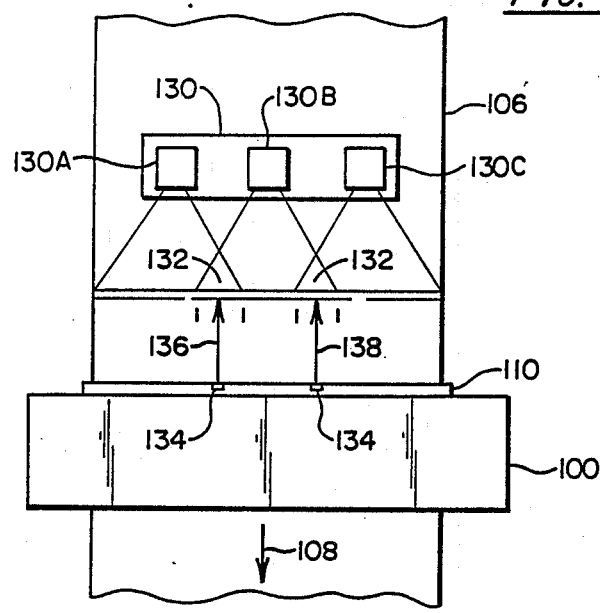
FIG. 3 is a schematic view of a video surface inspection system incorporating the light source module of the present invention and illustrating the overlapping fields of view of the individual cameras within a multi-camera array.

A video surface inspection system is shown schematically in FIG. 3 to illustrate the ability of the light source module 100 of the present invention to facilitate data processing by eliminating processing of redundant data generated by cameras of a multiple camera array 130 of the video surface inspection system. As shown in FIG. 3, the video cameras 130A, 130B, and 130C define overlapping fields of view such that the cameras image across the entire sheet 106. The overlaps 132 show that the camera 130A generates data which is also generated by the camera 130B which in turn generates data also generated by the camera 130C.

Since all this data must be processed at a sufficiently rapid rate to evaluate the surface of the sheet 106 which is the function of the video surface inspection system, and since the sheet 106 can move at a very rapid rate potentially exceeding 4500 fpm, this duplicate processing is detrimental to the operation of the video surface inspection system. While this processing problem can be overcome in software, it is a complicated procedure which in and of itself requires considerable computer time and is not entirely accurate.

To facilitate elimination of this dual data processing, the light source module 100 of the present invention provides second light emitter means which is adapted to illuminate the sheet 106 in each of a plurality of discontinuous regions corresponding to the overlaps 132 in the fields of view of adjacent cameras of a multi-camera array 130. In the illustrative embodiment, the second light emitter means comprises light emitting diodes 134 which are secured to the light guide 110 adjacent its light ejecting surface 120. Alternately, the second light emitter means could comprise light emitting diodes located adjacent the fluorescent lamps 104 or embedded in the light guide 110, optical fibers 135 as shown in FIG. 2, or other sources of light which serve to illuminate the sheet 106 within the overlaps 132 in the fields of view of adjacent cameras of the multi-camera array 130 as shown schematically in FIG. 3.

The light emitting diodes 134 or other light sources can be activated at the same time as the fluorescent lamps 104 and processed in real time to identify locations within the overlaps 132 as shown in FIG. 3 such that: data from the camera 130A would be processed only up to the point within the overlap 132 identified by the light beam arrow 136; data from the camera 130B would be processed only between points identified by the light beam arrow 136 and a light beam arrow 138; and, data from the camera 130C would only be processed if it was generated to the right of light beam arrow 138. In this way, the light source module 100 in accordance with the present invention facilitates elimination of the dual processing which is otherwise encountered due to the overlaps 132 between the fields of view of adjacent cameras of the multi-camera array 130.

Preferably, the secondary light emitter means, such as the light emitting diodes 134, is turned on during a standardization operation which is performed on the video surface inspection system on a periodic basis, and turned off during the normal operation of the inspection system. Such operation reduces the amount of real time processing required during the inspection of sheets and prevents any potential interference between inspection light from the fluorescent lamps 104 and the light emitting diodes 134 or other secondary light emitter used in accordance with the present invention.

Having described the invention in detail and by way of reference to preferred embodiments thereof, it will be apparent that other modifications and variations are possible without departing from the scope of the invention defined in the appended claims.

What is claimed is:

1. A light source module for use with a multi-camera array in inspecting a moving sheet of material, said light source module comprising:
   first light emitter means for emitting light in response to applied power, said first light emitter means extending lengthwise across the entire width of a sheet to be inspected as measured in a direction transverse to the direction of sheet movement;
   housing means supporting said first light emitter means which is secured thereto, said housing means extending lengthwise across a distance greater than the entire width of a sheet to be inspected; and
   light guide means secured to said housing means for receiving light from said first light emitter means and for guiding the received light toward a sheet to be inspected such than the sheet is illuminated over a portion thereof extending across its entire width, said light guide means having a light receiving surface facing said first light emitter means for direct reception of light therefrom and a light ejecting surface facing the sheet.

2. A light source module as claimed in claim 1 wherein said light guide means is composed of a transparent thermoplastic.

3. A light source module as claimed in claim 1 wherein said first light emitter means comprises at least one generally cylindrical fluorescent lamp having terminals on each end.

4. A light source module as claimed in claim 3 further comprising light control means connected to said first light emitter means for controlling the intensity of light emitted by said first light emitter means.

5. A light source module as claimed in claim 4 wherein said light control means comprises an inverter ballast connected to operate said at least one generally cylindrical fluorescent lamp and a variable dc power supply for driving said inverter ballast.

6. A light source module as claimed in claim 3 wherein said at least one fluorescent lamp is phosphor-coated over a first circumferential range thereof but not phosphor-coated over a second circumferential range.

7. A light source module as claimed in claim 3 wherein said first light emitter means comprises a plurality of such fluorescent lamps, said lamps being positioned in said housing means such that they axially extend in substantially the same direction and that the ends of adjacent pairs of said lamps overlap at least to a degree corresponding to the length of said terminals.

8. A light source module as claimed in claim 7 wherein said light guide means is composed of a transparent thermoplastic.

9. A light source module as claimed in claim 8 wherein the light receiving surface of said light guide means comprises a plurality of separate sections, each of said sections facing one of said plurality of fluorescent lamps and extending lengthwise in the axial direction of that lamp.

10. A light source module as claimed in claim 2 wherein the light receiving surface of said light guide means comprises a plurality of separate sections facing said first light emitter means.

11. A light source module as claimed in claim 10 wherein said first light emitter means comprises a plurality of generally cylindrical fluorescent lamps, each of said lamps having terminals on each end.

12. A light source module as claimed in claim 11 wherein each of the separate sections of said light guide means faces one of said lamps and extends lengthwise in the axial direction of said lamp.

13. A light source module as claimed in claim 12 wherein each lamp extends axially over a distance greater than the length of the corresponding separate section of the light receiving surface of said light guide means.

14. A light source module as claimed in claim 1 further comprising second light emitter means for emitting light in response to applied power, said second light emitter means being adapted to illuminate the sheet in each of a plurality of discontinuous regions corresponding to overlaps in the fields of view of adjacent cameras of the multi-camera array.

15. A light source module as claimed in claim 14 wherein said second light emitter means comprises a plurality of light-emitting diodes.

16. A light source module as claimed in claim 14 wherein said second light emitter means comprises a plurality of optical fibers.

17. A light source module as claimed in claim 14 wherein said first light emitter means comprises at least one generally cylindrical fluorescent lamp having terminals on each end.

18. A light source module as claimed in claim 17 further comprising light control means connected to said first light emitter means for controlling the intensity of light emitted by said first light emitter means.

19. A light source module as claimed in claim 18 wherein said light control means comprises an inverter ballast connected to operate said at least one generally cylindrical fluorescent lamp and a variable dc power supply for driving said inverter ballast.

20. A light source module as claimed in claim 17 wherein said first light emitter means comprises a plurality of such fluorescent lamps, said lamps being positioned in said housing means such that the lamps extend axially in substantially the same direction and such that the lamps of each adjacent pair thereof overlap at least to a degree corresponding to the length of the terminals.

21. A light source module as claimed in claim 20 wherein the light receiving surface of said light guide means has a plurality of separate sections, each section facing one of the fluorescent lamps and extending lengthwise in the axial direction of the lamp.

22. A light source module as claimed in claim 21 wherein said light guide means is composed of a transparent thermoplastic.

23. A light source module as claimed in claim 17 wherein said at least one fluorescent lamp is phosphor-coated over a first circumferential range thereof but not phosphor-coated over a second cirumferential range.

24. A light source module as claimed in claim 23 wherein the light receiving surface of said light guide means is aligned with the second circumferential range of the lamp so that the receiving surface faces the lamp at the second circumferential range thereof.

25. A light source module as claimed in claim 24 wherein said light guide means is composed of a transparent thermoplastic.

* * * * *